United States Patent [19]  [11] 4,017,635
Ishiguro  [45] Apr. 12, 1977

[54] MITICIDAL COMPOSITIONS COMPRISING 2-(P-TERT.-BUTYLPHENOXY)CYCLOHEXYL 2-PROPYNYL SULFITE AND DIBENZYL DISULFIDE

[75] Inventor: Takeo Ishiguro, Kusatsu, Japan

[73] Assignee: Shionogi & Co., Ltd., Osaka, Japan

[22] Filed: Mar. 21, 1975

[21] Appl. No.: 560,866

[30] Foreign Application Priority Data

Mar. 22, 1974 Japan .............................. 49-32943

[52] U.S. Cl. .............................. 424/303; 424/336
[51] Int. Cl.$^2$ ..................... A01N 9/02; A01N 9/12; A01N 9/14
[58] Field of Search ............................ 424/303, 336

[56] References Cited

UNITED STATES PATENTS 3,463,859  8/1969  Covey et al. ..................... 424/303

FOREIGN PATENTS OR APPLICATIONS 765,459  1/1957  United Kingdom

Primary Examiner—Jerome D. Goldberg
Assistant Examiner—Allen J. Robinson
Attorney, Agent, or Firm—Wenderoth, Lind & Ponack

[57] ABSTRACT

This invention relates to miticidal compositions. More particularly, it is directed to compositions comprising 2-(p-tert.-butylphenoxy)cyclohexyl 2-propynyl sulfite and dibenzyl disulfide. The compositions have a synergistic effect on adulticidal and ovicidal activities against a broad variety of mites.

2 Claims, No Drawings

MITICIDAL COMPOSITIONS COMPRISING 2-(P-TERT.-BUTYLPHENOXY)CYCLOHEXYL 2-PROPYNYL SULFITE AND DIBENZYL DISULFIDE

The invention relates to miticidal compositions comprising 2-(p-tert.butylphenoxy)cyclohexyl 2-propynyl sulfite (hereinafter called BPPS) and dibenzyl disulfide (hereinafter called DBDS) as active ingredients. Further, it relates to a process for preparing the same and a method for protecting plants (including a part of plants) from attack of mites which comprises applying the same to plants.

Parasitic insect pests, especially due to various strains belonging to mites, have been recognized as the major ones in the fields of crops, fruit trees and domestic animals. Particularly, they provide a heavy damage to various fruit trees such as apple, orange and pear trees, vegetables such as eggplants and cucumbers, and flowering horticultural plants such as carnations. Therefore, a great expense is required to control those insect pests every year in this field.

Many miticides have hitherto been employed. However, it has become very difficult to control the various mites by using of hitherto-known miticides, because they are very apt to acquire resistance to miticides as compared with other insect pests. Thus, the mite resistance has now become one of the most important problems in the field of control of mites in crops and fruit trees. To overcome the problems of the mite resistance, some measures have been proposed : (1) One is a continuous search for a new type of compound having a miticidal activity to keep the mites from acquiring resistance by substitution of the agents at short intervals and (2) the other is use of miticidal compositions comprising two or more active ingredients having a different mode of action.

In the course of research for new miticidal compositions comprising two or more active ingredients having a different mode of action against the mites, the inventor has discovered that mixtures of BPPS and DBDS have a synergistic effect on miticidal activity against broad strains of mites. The compounds, BPPS and DBDS, are well-known compounds having a miticidal action (U.S. Pat. No. 3,463,859 ; Japanese publication No. 8021/68 ). BPPS is mainly effective against adults and larvae of mites, and has the following structural formula:

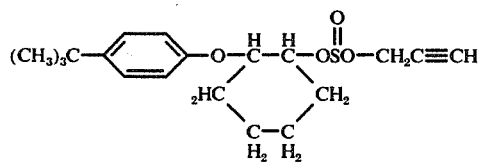

DBDS is mainly effective against eggs of mites, and has the following structural formula:

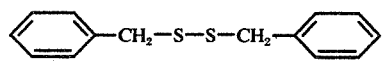

The combination of BPPS and DBDS markedly enhances miticidal activity of both active ingredients. Therefore, it is a characteristic aspect that the compositions of the invention show a synergistic effect on the miticidal activity simultaneously against adults, larvae and eggs of mites. Also, it is of significance that the compositions of the invention provide a significant reduction of hazards due to phytotoxicity, because they make it possible to substantially decrease the dosages required to control those mites which cause the major economic harm. Moreover, the compositions of the invention realize a substantial reduction in costs required to control mites. Thus, the present invention has been accomplished on the bases of these and other discoveries, and may be clearly characterized by its significant advantages in view of the aforesaid and other technical backgrounds.

Accordingly, a basic object of the invention is the provision of novel miticidal compositions comprising BPPS and DBDS as active ingredients. Another object of the invention is the provision of novel compositions having a synergistic effect on the miticidal activity against adults, larvae and eggs of mites. A further object of the invention is the provision of a process for preparing the same. A still further object of the invention is the provision of a method for protecting plants from attack of mites, which comprises applying the same to plants. These and other objects and the manner in which they are accomplished will become apparent to those conversant with the art from the following descriptions.

As stated above, the compositions of the invention comprise BPPS and DBDS as active ingredients. The compositions of the invention may be prepared by the combination of BPPS with DBDS in such proportions that they have a synergistic effect on the miticidal activity. For example, BPPS for convenience will ordinarily be combined with DBDS in the range of 1 to 100 parts of BPPS to 1 to 100 parts of DBDS. More preferred proportions are in the range of from 1 : 9 to 9 : 1 for the ratio of BPPS to DBDS. The compositions of the invention are well suited for control of a variety of mites including Family Tetranychidae, for example *Tetranychus cinnabarinus, Panonychus citri, Panonychus ulmi, Eotetranychus sexmaculatus, Eotetranychus kankitus, Tetranychus viennensis, Tetranychus urticae, Bryobia praetiosa, Bryobia rubrioculus, Eotetranychus smithi, Tetranychus kanzawai, Tetranychus desertorum;* Family Tenuipalpidae, for example *Brevipaltus lewisi, Tenuipalpus zhizhilashviliae;* Family Eriophyidae, for example *Aculus pelekassi, Calepitrimerus vitis;* Family Acaridae, for example *Rhizoglyphus echinopus;* Family Ixodidae; Family Pyroglyphidae and the like. In addition, the compositions of the invention have demonstrated high activity against various strains resistant to other miticides.

Preparation of the compositions of the invention may be ordinarily performed effectively if combined in the ways well known in the art for pesticidal formulations. The miticidal compositions of the present invention may be prepared in various conventional forms such as aerosols, solutions, emulsions, emulsifiable concentrates, wettable powders, pastes, dust, granules, pellets, tablets or the like according to the manner of use intended. The compositions may normally contain from about 0.1 percent by weight to about 90 percent by weight of BPPS and from about 0.1 percent by weight to about 90 percent by weight of DBDS as active ingredients, the amount depending on the form of composition as well as the manner of use intended. To formulate the compositions, suitable gaseous, liquid, or solid carriers and other ingredients including surface active agents are used in addition to BPPS and DBDS, and conventional techniques for mixing, blending, crushing, granulating, or tabletting may optionally be adopted. The surface active agents used in preparing the compositions of the present invention can be wetting, dispersing, or emulsifying agents. They may act, for example, as wetting agents for wettable powders and dust, as dispersing agents for wettable powders and suspensions, and as emulsifying agents for emulsions and emulsifiable concentrates. Suitable surface active agents for use in the compositions may be an anionic, non-ionic or cationic surface active agents. Such surface active agents are well known and reference may be made to U.S. Pat. No. 2,547,724, columns 3 and 4. For example, such surface active agents include polyethylene glycol esters with fatty acids; polyethylene glycol ethers with alkylphenols or with long-chain aliphatic alcohols; polyethylene glycol ethers with sorbitan fatty acid esters; polyoxyethylenethio ethers; polyoxyethylenealkylaryl ethers, ammonium, alkali, or alkaline earth salts of alkylaryl sulfonic acids; ammonium, alkali, or alkaline earth fatty alcohol sulfates; fatty acid esters of ammonium, alkali or alkaline earth isothionates or taurates; ammonium, alkali, or alkaline earth salts of lignin sulfonic acids; methylated or hydroxyethylated cellulose; polyvinyl alcohols; alkylsubstituted polyvinyl pyrrolidones; ammonium, alkali, or alkaline earth salts of polymerized alkylnaphthalene sulfonic acid; and long-chain quaternary ammonium compounds. Examples of the gaseous carrier include butane, nitrogen, carbon dioxide, Freon, and other inert gases. Liquid carriers for the present compositions may be water, or suitable inert organic solvent such as aliphatic hydrocarbons (e.g. pentane, hexane, cyclohexane, petroleum ether, gasoline, kerosene), aromatic hydrocarbons (e.g. benzene, toluene, xylene, naphtha), halogenated hydrocarbons (e.g. methylene chloride, chloroform, carbon tetrachloride, trichloroethane, ketones (e.g. acetone, methyl ethyl ketone, cyclohexanone), ethers (e.g. ether, isopropyl ether, tetrahydrofuran, dioxane), esters (e.g. ethyl acetate, amyl acetate) or alcohols (e.g. methanol, ethanol, butanol). Solid carriers may be, for example, mineral powders (e.g. clay, talc, mica, kaolin, bentonite, pyrophillite, diatomaceous earth, silica gel), vegetable powders (e.g. soybean powder, wheat powder) or other powders conventionally used as agricultural solid carriers or diluents.

More particularly, preferred forms of the compositions of the present invention for use may be solutions, emulsions, emulsifiable concentrates, wettable powders or dusts. The components of the composition of the invention may be admixed prior to formulation. For example, the compositions of BPPS and DBDS may be formulated as wettable powders, emulsifiable concentrates, dusts and the like. Two active ingredients (BPPS and DBDS) may be uniformly admixed with a surface active agents and a suitable solvent to prepare an emulsifiable concentrate. Two active ingredients may be uniformly admixed with a surface active agent, a dispersing agent and a carrier such as a fine mineral powder, subsequently ground to prepare a fine compositions in the form of wettable powder. Two active ingredients with a fine mineral powder are blended to a uniform mixture. The obtained dust can be used for application.

In addition, each active component may be independently formulated, and the resultant compositions may be admixed to obtain the intended formulation. For example, wettable powders or emulsifiable concentrates of BPPS may be admixed with wettable powders, emulsifiable concentrate or solution formulations of DBDS. The resultant mixture can be diluted with water and dispersed with agitation so that a uniform application results.

If desired, the compositions of the present invention may contain, in addition to BPPS and DBDS, other miticides, plant-regulants, plant hormones, germicides, insecticides, fungicides, nematocides, herbicides, fertilizers and/or the like.

The various formulations of the compositions of the invention described above can be applied by suitable means well known in the art. Methods and rates of application will be determined in accordance with the intended use and are, of course, influenced by the species of mite to be controlled, their stage in the life cycle, the manner of treatment, and the weather conditions prevalent during the application.

The rate of application may be expressed in several different ways. Ordinarily for crops growing in the field it is customary and convenient to express dosages in terms of weight per unit of field area treated. The total active chemical amounts employed for the compositions of the invention will usually range from 20 to 0.25 kilograms per hectare. However, for convenience and economy, the rate will ordinarily range from 4 to 0.2 kilograms per hectare and preferably from 2 to 0.2 kilograms per hectare of combined active ingredients.

Another manner of expressing the rate of application of the compositions of the invention is the unit of weight of active ingredients per given volume of water in the resulting solution, suspension or emulsion when used to spray the mite to be controlled or the locus thereof. Expressed in these terms, the total amount of active chemical employed in the compositions of the invention ranges from 400 to 25 grams per 100 liters of water. Again for reasons of economy and convenience the range will ordinarily be from 200 to 50 grams per 100 liters of water.

The test data which follow will serve to make it clear that the compositions of the present invention have excellent activity in terms of synergistic effect.

EXPERIMENT 1

Test of the ovicidal effect of the compositions comprising BPPS and DBDS, and those comprising a single active ingredient against the eggs of *Tetranychus cinnabarinus*.

(1) Compositions used in test: BPPS: 30% wettable powder sold by Shionogi & Co., Ltd. under the Tradename "Shionogi - Omite" was used.

DBDS: Preparation of DBDS solution. DBDS sold by Nakarai Kagakuyakushin Company was dissolved in a small amount of N,N-dimethylformamide, and to the solution was added distilled water containing 1000 ppm of Tween 20.

Preparation of 10 % emulsifiable concentrate of DBDS. (part by weight)
DBDS — 1 part
Xylene — 5 parts
"Sorpol-50" (Trade Mark) — 1 part
Tween 20 — 1 part
Dimethylformamide — 2 parts.
Compositions of BPPS and DBDS:

30 % wettable powder of "Shionogi-Omite" was diluted, and the formulation of DBDS was added to the solution to make the desired concentrations.

(2) Method for experiment.

A leaf (1.8 cm in diameter) of Kidney bean placed on wet filter paper was infested with 7–8 female adults of Tetranychus cinnabarinus, and was kept at 25° C overnight so as to permit them to lay eggs on the surface of the leaf. After the adults were removed, the thus prepared leaves having eggs thereon were sprayed with 2 ml (per leaf) of a dilute solution containing the chemicals at various concentrations within 24 hours after oviposition. Then, the leaves were kept at 25° C. When the larvae which had hatched from eggs in the untreated plot grew to prenymph period (about 7–8 days after the treatment), the hatching of eggs on the leaves was examined in the untreated and the treated plots.

(3) Results.

The results are shown in Table 1.

(4) Discussion.

The compositions of BPPS (150 ppm) and DBDS (50 ppm or more) show a markedly higher ovicidal activity against eggs of Tetranychus cinnabarimus than those comprising the single active ingredient.

Experiment 2

Test of the ovicidal effect of the compositions comprising BPPS and DBDS, and those comprising a single active ingredient against eggs of Tetranychus urticae.

(1) Compositions used for test.

The compositions are prepared according to the manner as described in the experiment 1.

(2) Method for experiment.

The experiment was carried out according to the manner as described in the experiment 1.

Table 1

| Formulation | Concentration of DBDS (ppm) | Composition comprising single active ingredient (DBDS) BPPS 0 ppm | | Composition comprising two active ingredients (BPPS and DBDS) BPPS 150 ppm | |
|---|---|---|---|---|---|
| | | Number of egg | Ovicidal rate (%) | Number of egg | Ovicidal rate % |
| Solution of DBDS | 200 | 183 | 79.2 | 128 | 99.2 |
| | 100 | 191 | 34.6 | 166 | 72.3 |
| | 50 | 157 | 22.3 | 176 | 35.8 |
| | 25 | 167 | 12.0 | 169 | 15.4 |
| | 12.5 | 156 | 10.3 | 186 | 4.3 |
| 10 % emulsifiable concentrate of DBDS | 200 | 170 | 88.2 | 173 | 96.0 |
| | 100 | 123 | 37.4 | 152 | 65.8 |
| | 50 | 158 | 14.6 | 137 | 37.2 |
| | 25 | 150 | 10.7 | 153 | 12.4 |
| | 12.5 | 164 | 4.9 | 144 | 8.3 |
| Control | 0 | 172 | 1.2 | 149 | 11.4 |

(3) Results. The results are shown in Table 2.

(4) Discussion.

The compositions comprising DBDS (18.8 ppm) and BPPS (18.8 ppm or 75 ppm) have a synergistic effect on the ovicidal activity against Tetranychus urticae.

Experiment 3

Test of adulticidal effect of the compositions comprising BPPS and DBDS, and those comprising a single active ingredient against the adults of Tetranychus cinnabarinus.

(1) Compositions used for test. The compositions are prepared according to the manner as described in the experiment 1.

(2) Method for experiment.

A leaf (1.8 cm in diameter) of Kidney bean was infested with 15 adult mites (Tetranychus cinnabarinus), and then kept at 25° C overnight. Dead and weak adult mites were removed from the leaf to keep only the healthy adult mites on it. The thus prepared leaves were sprayed with 4 ml (per leaf) of the compositions comprising BPPS and DBDS or those of the single active component, and kept at 25° C. Counting the number of dead mites was effected after 24 and 48 hours.

(3) Results. The adulticidal effects of the compositions are shown in Table 3.

(4) Discussion.

The compositions comprising BPPS and DBDS, particularly at the concentration 18.8 ppm of BPPS, show a synergistic effect on an adulticidal activity against Tetranychus cinnabarinus.

Table 2

| Egg of Mite | Concentration of DBDS (ppm) | Concentration of BPPS | | | | | | | |
|---|---|---|---|---|---|---|---|---|---|
| | | 0 ppm | | 300 ppm | | 75 ppm | | 18.8 ppm | |
| | | Number of egg | Ovicidal rate (%) | Number of egg | Ovicidal rate (%) | Number of egg | Ovicidal rate (%) | Number of egg | Ovicidal rate (%) |
| Tetranychus urticae | 300 | 266 | 99.6 | 191 | 100 | 171 | 100 | 181 | 100 |
| | 150 | 192 | 98.4 | 225 | 99.6 | 245 | 99.2 | 173 | 100 |
| | 75 | 207 | 89.9 | 198 | 100 | 219 | 97.3 | 235 | 97.0 |
| | 37.5 | 182 | 56.0 | 189 | 98.4 | 258 | 82.6 | 223 | 52.0 |
| | 18.8 | 233 | 10.7 | 183 | 96.0 | 229 | 76.0 | 225 | 53.0 |
| | 0 | 208 | 0.5 | 224 | 86.2 | 241 | 10.4 | 247 | 0.8 |

Table 3

| Formulation | Concentration (ppm) | 37.5 ppm | | | 18.7 ppm | | | 9.4 ppm | | | 0 ppm | | |
|---|---|---|---|---|---|---|---|---|---|---|---|---|---|
| | | Number of mites | Adulticidal rate (%) 24 hr | 48 hr | Number of mites | Adulticidal rate (%) 24 hr | 48 hr | Number of mites | Adulticidal rate (%) 24 hr | 48 hr | Number of mites | Adulticidal rate (%) 24 hr | 48 hr |
| 10 % emulsifiable concentrate of DBDS | 0 | 44 | 86.4 | 97.5 | 55 | 21.8 | 45.1 | 55 | 9.1 | 20.0 | 56 | 5.4 | 11.5 |
| | 100 | 42 | 95.2 | 100 | 45 | 50.0 | 77.8 | 55 | 16.4 | 30.8 | 51 | 7.8 | 14.9 |
| | 200 | 35 | 97.1 | 100 | 45 | 48.9 | 69.8 | 45 | 17.8 | 33.3 | 49 | 4.1 | 10.9 |
| | 400 | 41 | 97.6 | 100 | 32 | 59.4 | 75.9 | 48 | 20.8 | 34.0 | 50 | 10.0 | 12.2 |

The following examples are given solely for the purpose of illustration and are not to be construed as limiting this invention, many variations of which are possible. (Parts used in these examples are in terms of "by weight".)

EXAMPLE 1

An emulsifiable concentrate is prepared as follows:
BPPS—25 parts
DBDS—25 parts
Xylene—30 parts
Surface active agent such as polyoxyethylenealkylaryl ether—20 parts Two active ingredients are mixed with xylene, and the surface active agent is added and blended to obtain a homogenous mixture.

Two emulsifiable concentrate is added to water at the rate of 100 milliliters of solution (50 grams of total active ingredients) per 100 liters. The resulting aqueous suspension is applied by spraying 3 times at intervals of 14 days to apple trees. The trees sprayed with the above emulsifiable concentrate show a marked decrease in damage caused by the adults of Panonychus ulmi.

EXAMPLE 2

A wettable powder is prepared as follows:
BPPS—20–10 parts
DBDS—10 –20 parts
Diatomaceous earth—65 parts
Sodium lignin sulfonate—2 parts
Sodium alkylbenzene sulfonate—3 parts Two active ingredients are blended with diatomaceous earth, the other ingredients are added, and blended to a homogeneous mixture. Then the composition is finely ground.

The wettable powder is added to water at the rate of 100 grams of powder (40 grams of total active ingredients) per 100 liters. The resulting aqueous suspension is applied by spraying twice at intervals of 14 days to orange trees. The trees sprayed with the above wettable powder show a marked decrease in damage caused by the adults of *Panonychus citri*.

EXAMPLE 3

A wettable powder is prepared as follows:
BPPS — 15 parts
DBDS — 5 parts
Diatomaceous earth — 20 parts
Kaolin — 42.5parts
Mixture of sodium lauryl sulfate and disodium dinaphthylmethanedisulfonate — 7.5 parts Two active ingredients are mixed with the diatomeaceous earth, the other ingredients are added, and blended to a homogenous mixture. Then, the composition is finely ground.

The wettable powder is added to water at the rate of 200 grams of powder (40 grams of total active ingredients) per 100 liters. The resulting aqueous suspension is applied by spraying 3 times at intervals of 14 days to apple trees. The trees sprayed with the above wettable powder show a marked decrease in damage caused by the larvae of *Panonychus ulmi*.

EXAMPLE 4

A dust is prepared as follows:
BPPS — 3–7 parts
DBDS — 7–3 parts
Talc — 90 parts The composition is prepared by blending the said ingredients, which are subsequently finely ground.

The dust is applied at intervals of 7 days at the rate of 100 Kg per hectare to orange trees to be infected with eggs of *Panonychus citri*. The eggs are markedly killed 14 days after application.

What is claimed is:

1. A miticidal composition comprising a miticidally effective amount of a mixture of 2-(p-tert.-butylphenoxy)cyclohexyl 2-propynyl sulfite and dibenzyl disulfide in a weight ratio for the sulfite to the disulfide of from 18.8 : 75 to 75 : 18.8.

2. A method for protecting plants from attack of mites which comprises applying a miticidally effective amount of the composition as defined in claim 1 to the plants.

* * * * *